(12) United States Patent  
McDonald et al.

(10) Patent No.: US 8,868,207 B2  
(45) Date of Patent: Oct. 21, 2014

(54) SYSTEMS AND METHODS FOR MAKING AND USING ELECTRICAL STIMULATION SYSTEMS WITH IMPROVED RF COMPATIBILITY

(75) Inventors: Matthew Lee McDonald, Pasadena, CA (US); Ross Daniel Venook, Millbrae, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 96 days.

(21) Appl. No.: 13/357,910

(22) Filed: Jan. 25, 2012

(65) Prior Publication Data

US 2012/0191167 A1 Jul. 26, 2012

Related U.S. Application Data

(60) Provisional application No. 61/436,280, filed on Jan. 26, 2011.

(51) Int. Cl.
*A61N 1/18* (2006.01)
*A61N 1/05* (2006.01)
*A61N 1/08* (2006.01)

(52) U.S. Cl.
CPC ............ *A61N 1/05* (2013.01); *A61N 2001/086* (2013.01)
USPC ........................................... 607/116; 607/63

(58) Field of Classification Search
CPC .............................................. A61N 2001/086
USPC .................. 607/63, 115–117, 119, 121, 122; 600/372–374, 377, 378
See application file for complete search history.

(56) References Cited

U.S. PATENT DOCUMENTS

| 5,217,010 | A | | 6/1993 | Tsitlik et al. |
| 5,796,044 | A | * | 8/1998 | Cobian et al. ................. 174/103 |

(Continued)

FOREIGN PATENT DOCUMENTS

WO  03-063946 A2  8/2003

OTHER PUBLICATIONS

Rezai, A.R. et al., "Neurostimulation system used for deep brain stimulation (DBS): MR safety issues and implications of failing to follow safety recommendations," Investigative Radiology, vol. 39, No. 5, 2004, pp. 300-303.

(Continued)

*Primary Examiner* — Carl H Layno
*Assistant Examiner* — Eugene Wu
(74) *Attorney, Agent, or Firm* — Lowe Graham Jones PLLC; Patrick R. Turner

(57) ABSTRACT

An implantable electrical stimulation lead includes a plurality of conductors that extend along a lead body and that electrically couple electrodes to terminals. A first tissue coupler is electrically coupled to a first conductor of the plurality of conductors. The first tissue coupler includes a conductive first inner member, a non-conductive member disposed adjacent to at least a portion of the first inner member, and a conductive outer member disposed adjacent to at least a portion of the non-conductive member such that at least a portion of the non-conductive member is sandwiched between the first inner member and the outer member. The first inner member is electrically coupled to the first conductor. The outer member is disposed along a portion of an outer surface of the lead body such that the conductive outer member is exposed to patient tissue when the lead is implanted in a patient.

20 Claims, 8 Drawing Sheets

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,944,489 B2 * | 9/2005 | Zeijlemaker et al. ......... 600/373 |
| 7,244,150 B1 | 7/2007 | Brase |
| 7,363,090 B2 * | 4/2008 | Halperin et al. ............. 607/116 |
| 7,672,734 B2 | 3/2010 | Anderson |
| 7,761,165 B1 | 7/2010 | He |
| 7,949,395 B2 | 5/2011 | Kuzma |
| 7,974,706 B2 | 7/2011 | Moffitt |
| 8,032,230 B1 * | 10/2011 | Cox et al. ...................... 607/116 |
| 8,275,464 B2 * | 9/2012 | Li et al. ........................... 607/63 |
| 2003/0083726 A1 | 5/2003 | Zeijlemaker et al. |
| 2005/0165465 A1 | 7/2005 | Pianca |
| 2005/0256557 A1 * | 11/2005 | Wessman et al. ............. 607/116 |
| 2006/0247684 A1 | 11/2006 | Halperin et al. |
| 2006/0247748 A1 * | 11/2006 | Wahlstrand et al. .......... 607/116 |
| 2007/0150036 A1 | 6/2007 | Anderson |
| 2007/0219595 A1 | 9/2007 | He |
| 2008/0033497 A1 * | 2/2008 | Bulkes et al. ..................... 607/9 |
| 2008/0071320 A1 | 3/2008 | Brase |
| 2008/0243218 A1 * | 10/2008 | Bottomley et al. ........... 607/116 |
| 2009/0149920 A1 * | 6/2009 | Li et al. ........................... 607/63 |
| 2010/0076508 A1 | 3/2010 | McDonald |
| 2010/0094364 A1 | 4/2010 | McDonald |
| 2010/0191236 A1 * | 7/2010 | Johnson et al. ................. 606/41 |
| 2010/0256693 A1 | 10/2010 | McDonald |
| 2010/0326701 A1 | 12/2010 | McDonald |
| 2011/0009932 A1 | 1/2011 | McDonald |
| 2011/0046700 A1 | 2/2011 | McDonald |

OTHER PUBLICATIONS

Nyenhuis, J.A. et al., "MRI and implanted medical devices: basic interactions with an emphasis on heating," IEEE Transactions on Device and Materials Reliability, vol. 5, No. 3, 2005, pp. 467-480.
International Search Report & Written Opinion, International Application No. PCT/US2012/022528 mailed Jun. 6, 2013.

* cited by examiner

SYSTEMS AND METHODS FOR MAKING AND USING ELECTRICAL STIMULATION SYSTEMS WITH IMPROVED RF COMPATIBILITY

CROSS-REFERENCE TO RELATED APPLICATIONS

This application claims the benefit under 35 U.S.C. §119(e) of U.S. Provisional Patent Application Ser. No. 61/436,280 filed on Jan. 26, 2011, which is incorporated herein by reference.

FIELD

The present invention is directed to the area of implantable electrical stimulation systems and methods of making and using the systems. The present invention is also directed to implantable electrical stimulation leads or lead extensions that include elements for reducing susceptibility to RF irradiation during exposure to RF radiation, as well as methods of making and using the leads, lead extensions, RF-irradiation-susceptibility-reducing elements, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, an implantable electrical stimulation lead includes a lead body having a distal end, a proximal end, a longitudinal length, and an outer surface. A plurality of electrodes are disposed on the distal end of the lead body. A plurality of terminals are disposed on the proximal end of the lead body. A plurality of conductors electrically couple at least one of the electrodes to at least one of the terminals, the plurality of conductors extending along the longitudinal length of the lead body. A first tissue coupler is electrically coupled to a first conductor of the plurality of conductors. The first tissue coupler includes a conductive first inner member, a non-conductive member disposed adjacent to at least a portion of the first inner member, and a conductive outer member disposed adjacent to at least a portion of the non-conductive member such that at least a portion of the non-conductive member is sandwiched between the first inner member and the outer member. The first inner member is electrically coupled to the first conductor. The outer member is disposed along a portion of the outer surface of the lead body such that the outer member is exposed to patient tissue when the lead is implanted in a patient.

In another embodiment, an electrical stimulation system includes a lead body having a distal end, a proximal end, a longitudinal length, and an outer surface. A plurality of electrodes are disposed on the distal end of the lead body. A plurality of terminals are disposed on the proximal end of the lead body. A plurality of conductors electrically couple at least one of the electrodes to at least one of the terminals, the plurality of conductors extending along the longitudinal length of the lead body. A first tissue coupler is electrically coupled to a first conductor of the plurality of conductors. The first tissue coupler includes a conductive first inner member, a non-conductive member disposed adjacent to at least a portion of the first inner member, and a conductive outer member disposed adjacent to at least a portion of the non-conductive member such that at least a portion of the non-conductive member is sandwiched between the first inner member and the outer member. The first inner member is electrically coupled to the first conductor. The outer member is disposed along a portion of the outer surface of the lead body such that the outer member is exposed to patient tissue when the lead is implanted in a patient. A control module is configured and arranged to electrically couple to the proximal end of the lead body. The control module includes a housing and an electronic subassembly disposed in the housing. A connector is configured and arranged to receive the lead. The connector has a proximal end, a distal end, and a longitudinal length. The connector includes a connector housing defining a port at the distal end of the connector that is configured and arranged for receiving the proximal end of the lead body. A plurality of connector contacts are disposed in the connector housing and are configured and arranged to couple to at least one of the plurality of terminals disposed on the proximal end of the lead body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads or lead extensions that include elements for reducing susceptibility to RF irradiation during exposure to RF radiation, as well as methods of making and using the leads, lead extensions, RF-irradiation-susceptibility-reducing elements, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; and 7,974,706; and U.S. Patent Applications Publication Nos. 2005/0165465, 2007/0150036; 2007/0219595, all of which are incorporated by reference.

Figure 1:
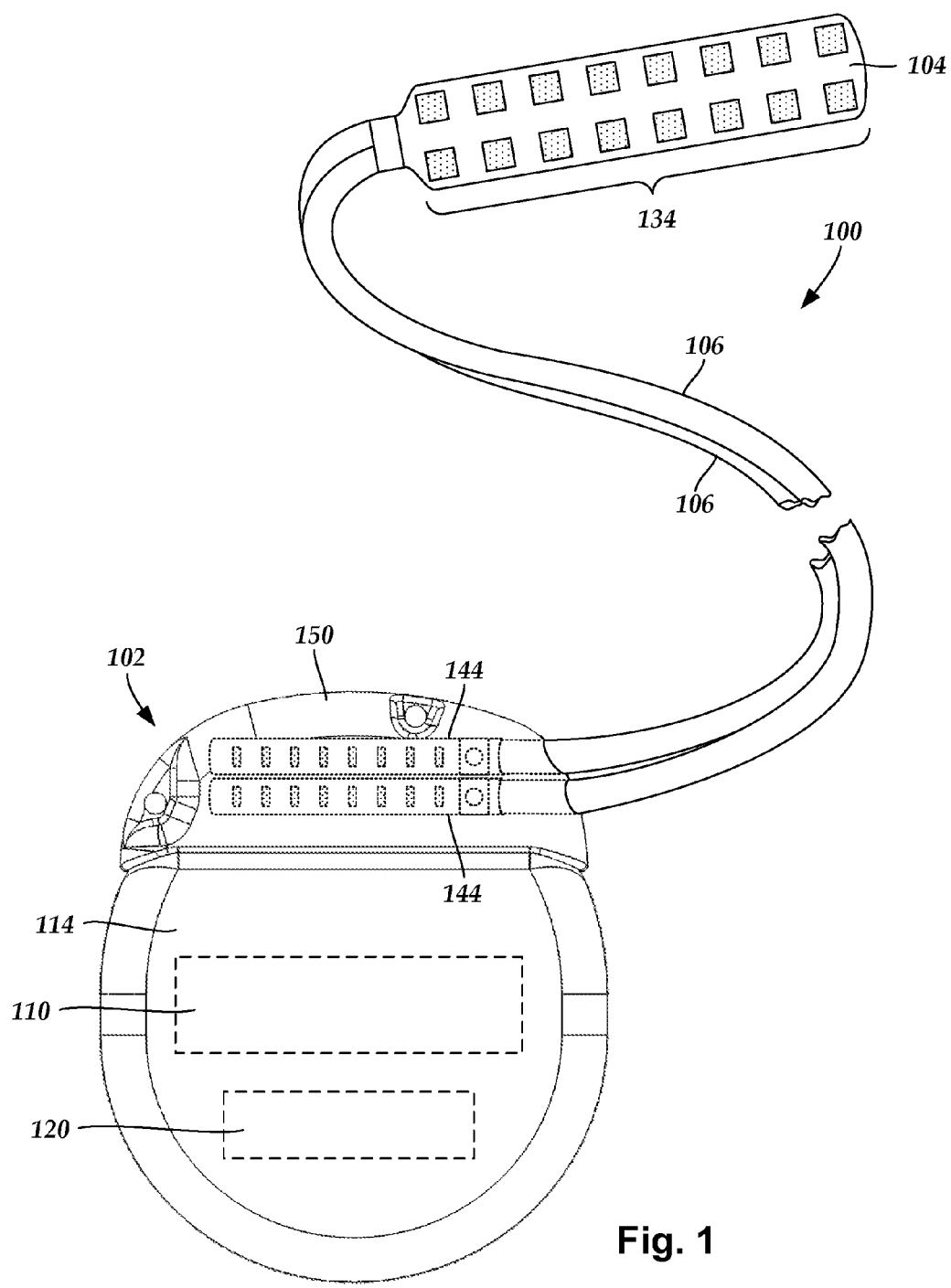
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIGS. 3A-3B; and 340 of FIG. 3C) disposed in the connector assembly 144 and terminals (e.g., 310 in FIGS. 3A-3C) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
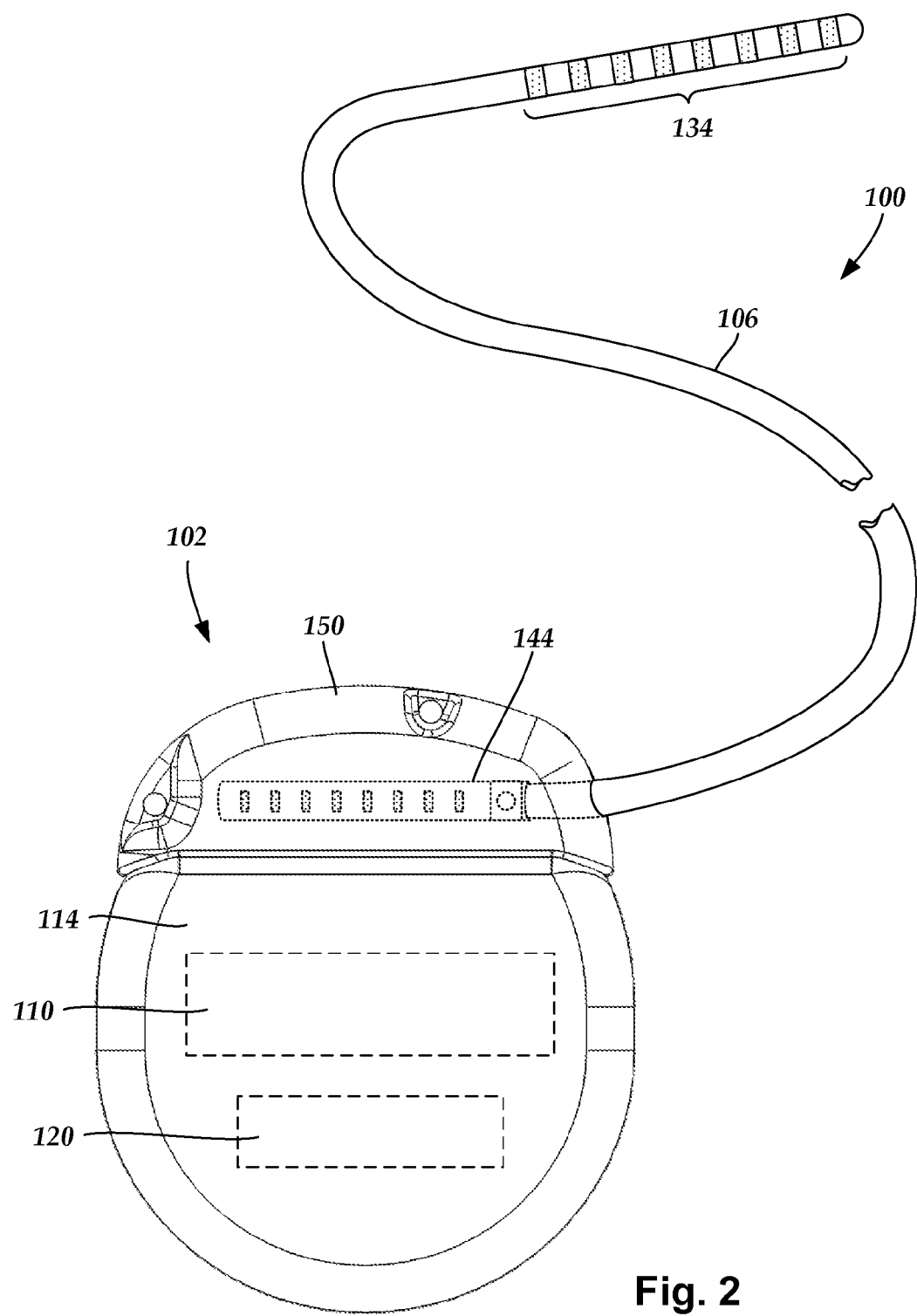
FIG. 2 is a schematic view of another embodiment of an electrical stimulation system that includes a percutaneous lead body coupled to the control module of FIG. 1, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead body 106.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 134 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIGS. 3A-3C) are typically disposed at the proximal end of the one or more lead bodies 106 for connection to corresponding conductive contacts (e.g., 316 in FIGS. 3A-3B; and 340 of FIG. 3C) in connector assemblies (e.g., 144 in FIGS. 1-3C) disposed on, for example, the control module 102 (or to other devices, such as conductive contacts on a lead extension, an operating room cable, a splitter, an adaptor, or the like).

Conductive wires (not shown) extend from the terminals (e.g., 310 in FIGS. 3A-3C) to the electrodes 134. Typically, one or more electrodes 134 are electrically coupled to a terminal (e.g., 310 in FIGS. 3A-3C). In some embodiments, each terminal (e.g., 310 in FIGS. 3A-3C) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more stylet lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
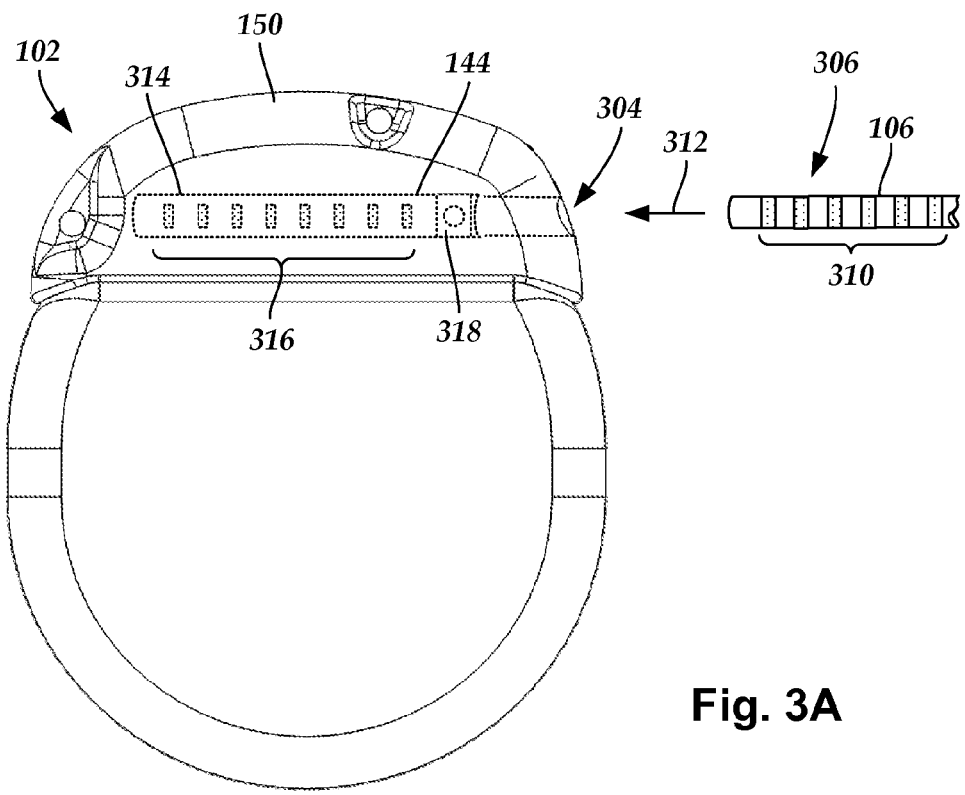
FIG. 3A is a schematic view of one embodiment of a connector assembly disposed in the control module of FIG. 1, the connector assembly configured and arranged to receive the proximal portion of one of the lead bodies of FIG. 1, according to the invention.
Figure 3B:
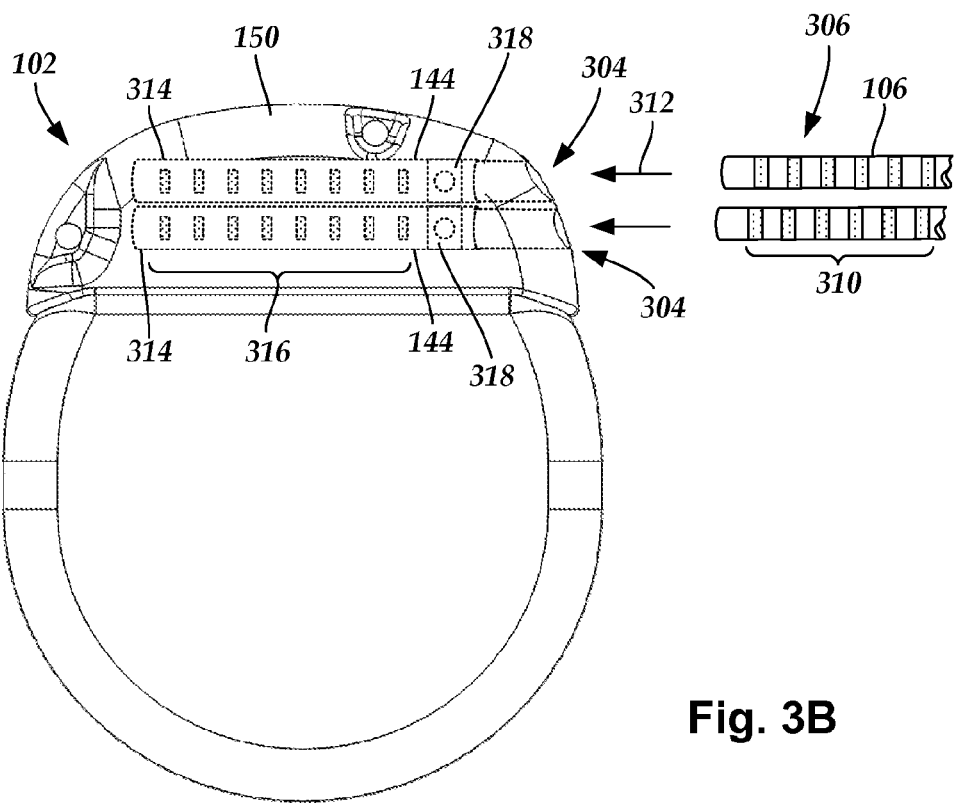
FIG. 3B is a schematic view of one embodiment of a plurality of connector assemblies disposed in the control module of FIG. 1, the connector assemblies configured and arranged to receive the proximal portions of the lead bodies of FIG. 1, according to the invention.

In at least some embodiments, leads are coupled to connectors disposed on control modules. FIG. 3A is a schematic perspective view of one embodiment of a single connector assembly 144 disposed on the control module 102. FIG. 3B is a schematic perspective view of one embodiment of a plurality of connector assemblies 144 disposed on the control module 102. In at least some embodiments, the control module 102 includes two connector assemblies 144. In at least some embodiments, the control module 102 includes four connector assemblies 144. In FIGS. 3A and 3B, the proximal ends 306 of one or more lead bodies 106 are shown configured and arranged for insertion to the control module 102. In FIGS. 3A and 3B, the one or more connector assemblies 144 are disposed in the header 150. In at least some embodiments, the header 150 defines one or more ports 304 into which a proximal end 306 of the one or more lead bodies 106 with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 308 to the connector assembly 144 when the lead body 106 is inserted into the connector assembly 144 to prevent undesired detachment of the lead body 106 from the connector assembly 144. For example, the retaining element 318 may include an aperture through which a fastener (e.g., a set screw, pin, or the like) may be inserted and secured against an inserted lead body or lead extension.

When the one or more lead bodies 106 are inserted into the one or more ports 304, the connector contacts 316 can be aligned with the terminals 310 disposed on the one or more lead bodies 106 to electrically couple the control module 102 to the electrodes (134 of FIG. 1) disposed at a distal end of the one or more lead bodies 106. Examples of connector assemblies in control modules are found in, for example, U.S. Pat. No. 7,244,150 and U.S. Patent Application Publication No. 2008/0071320 A1, which are incorporated by reference.

Figure 3C:
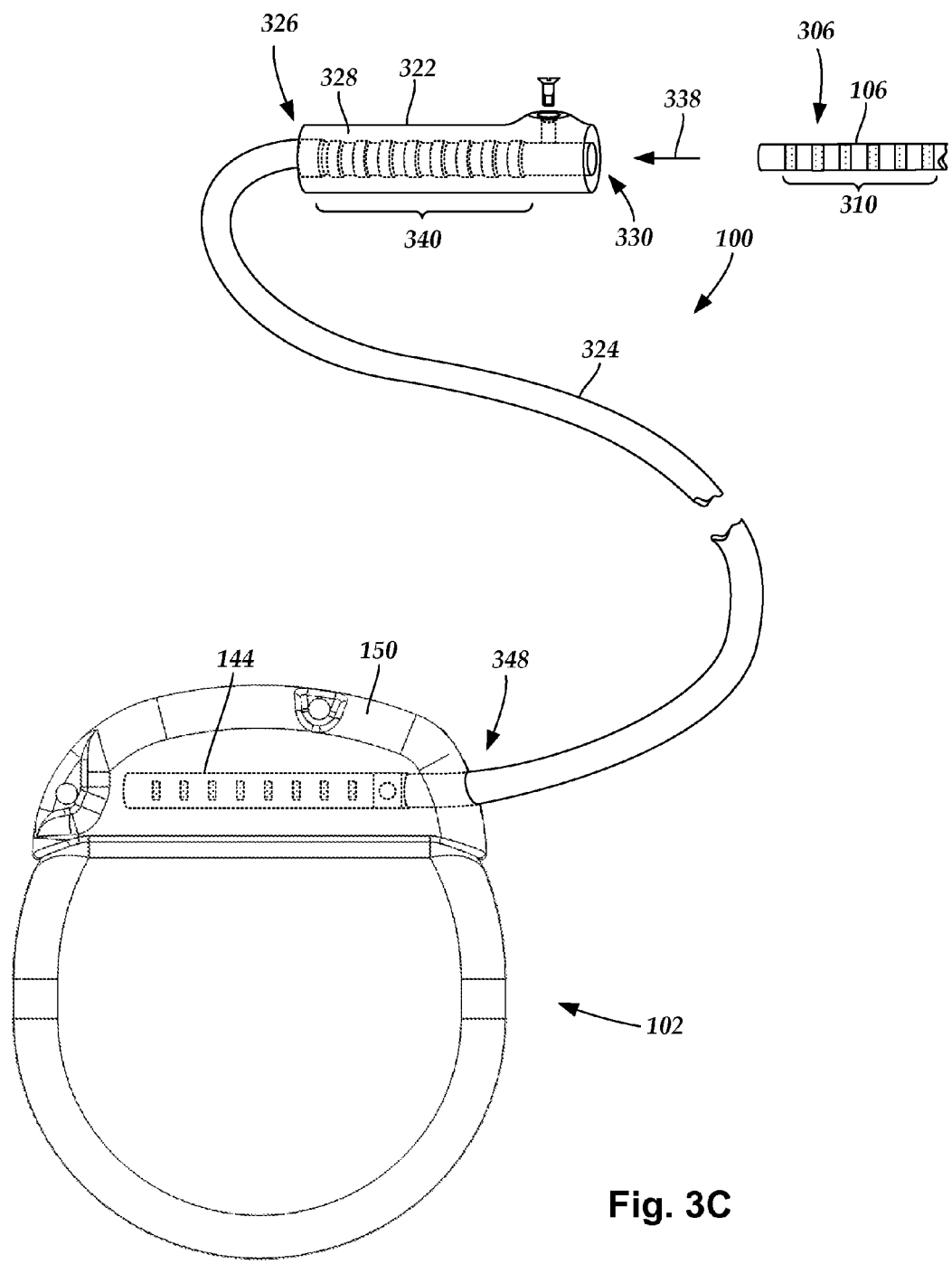
FIG. 3C is a schematic view of one embodiment of a proximal portion of one of the lead bodies of FIG. 1, a lead extension, and the control module of FIG. 1, the lead extension configured and arranged to couple the lead body to the control module, according to the invention.

In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106 with terminals 310 can be inserted, as shown by directional arrow 338. The lead extension connector assembly 322 also includes a plurality of connector contacts 340. When the lead body 106 is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106.

The proximal end of a lead extension can be similarly configured and arranged as a proximal end of a lead body. The lead extension 324 may include a plurality of conductive wires (not shown) that electrically couple the connector contacts 340 to a proximal end 348 of the lead extension 324 that is opposite to the distal end 326. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102.

Conventional electrical stimulation systems may be potentially unsafe for use when exposed to RF irradiation, such as during a magnetic resonance imaging ("MRI") procedure. A common cause of the electrical interaction between the electrical stimulation system and RF irradiation is common-mode coupling of the applied electromagnetic field. The interaction can be modeled as a series of distributed sources along the elongated conductive structures of the electrical stimulation system, such as leads, or conductors within leads. Common-mode induced RF currents may reach amplitudes of greater than one ampere in MRI environments. Such currents can cause heating and potentially disruptive voltages within electronic circuits.

Figure 4:
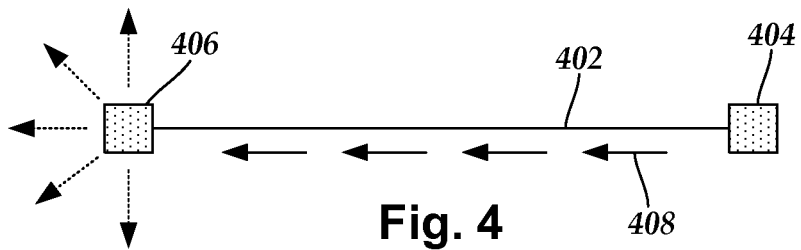
FIG. 4 is a schematic side view of one embodiment of a common-mode current propagating along an exemplary conductor of a lead.

FIG. 4 is a schematic diagram of one embodiment of a conductor 402 suitable for use in a lead (or lead extension). The conductor 402 extends between a terminal 404 and an electrode 406 (or a connector contact). When the conductor 402 is exposed to RF irradiation, such as when an implanted conductor 402 is in a patient undergoing an MRI procedure, a distributed electrical source (e.g., current, voltage), represented in FIG. 4 as arrows 408, can be formed and distributed along the conductor 402 by the coupling of incident electrical fields within the conductor 402.

The electrical fields can become concentrated at the ends of the conductor 402, such as the terminal 404 and the electrode 406 (or connector contact), causing one or more undesired effects. Some of the undesired effects may include, for example, excessive heating that may potentially cause tissue damage, induced currents (potentially causing heating, undesired electrical stimulation, or device malfunction), undesired or unexpected operation of electronic components, or premature failure of electronic components.

To reduce the susceptibility of the electrical stimulation system to undesired RF irradiation, one or more antenna properties (e.g., the ability to receive energy at certain frequencies from external electromagnetic fields), electromagnetic properties (e.g., inductance, capacitance, permittivity, or the like), or both, can be altered along a length of the lead (or lead extension). As herein described, one or more RF-irradiation-susceptibility-reducing elements ("elements") are incorporated into the lead (or lead extension). The elements can reduce susceptibility of the electrical stimulation system to RF irradiation in different ways including, for example, coupling one or more of the conductors of the lead (or lead extension) to patient tissue, altering the antenna properties of one or more of the conductors, or mimicking one or more circuit elements (e.g., capacitors, inductors, transformers, or the like) for reducing propagation of undesired energy along a length of the lead (or lead extension).

The elements can include, for example, one or more tissue couplers. When the lead (or lead extension) is implanted in the patient, the one or more tissue couplers can couple patient tissue to one or more of the conductors extending along the lead (or lead extension) between at least one electrode (or connector contact) and at least one terminal. The tissue couplers are at least partially exposed to patient tissue at a frequency (or frequency range) of interest along an outer surface of the lead body (or lead extension body). The tissue couplers, optionally, include one or more capacitive elements that selectively favor propagation of energy at certain frequencies (or frequency ranges) across the one or more capacitive elements to contact patient tissue, while disfavoring propagation of energy at other frequencies.

The elements can include, for example, one or more inductive elements disposed along the length of the lead (or lead extension). The inductive elements (as well as the capacitive elements) can be used to break up induced standing waves. Two or more different elements (e.g., capacitive elements, inductive elements, and the like) can be used in various combinations to achieve desired properties.

Figure 5:
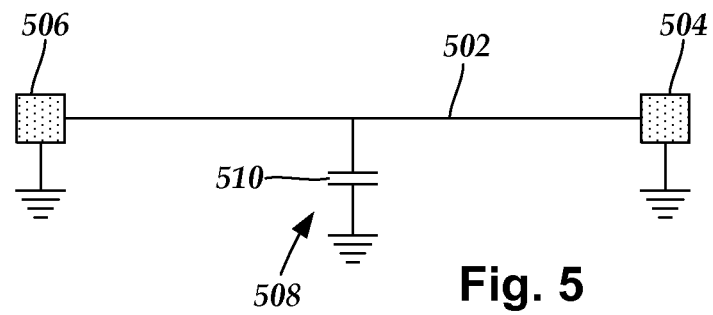
FIG. 5 is a schematic diagram of one embodiment of a tissue coupler coupled to a conductor, the tissue coupler enabling at least some energy propagating along the conductor to escape along the tissue coupler, according to the invention.

FIG. 5 is a schematic diagram of one embodiment of a conductor 502 extending between a terminal 504 and an electrode 506 (or connector contact). A tissue coupler 508 is coupled to the conductor 502 at any suitable location along a length of the conductor 502 between the terminal 504 and the electrodes 506 (or connector contacts). It will be understood that the lead (or lead extension) can include any suitable number of conductors (e.g., one, two, three, four, five, six, seven, eight, nine, ten, eleven, twelve, thirteen, fourteen, fifteen, sixteen, or more). It will be understood that the conductor 502 can extend in any suitable arrangement including, for example, substantially straight (e.g., forming less than one revolution around the stylet lumen 610), or any suitable coiling configuration arranged into any suitable number of layers (see e.g., FIGS. 7 and 9).

The tissue coupler 508 enables at least some energy to escape from the conductor 502 without propagating to the terminal 204, the electrode 506 (or connector contact), or both. In at least some embodiments, a plurality of tissue couplers 508 can be coupled to one or more of the conductors 502 such that, when the conductors 502 are disposed in the lead (or lead extension), the plurality of tissue couplers 508 are axially disposed along the length of the lead (or lead extension). When a plurality of tissue couplers 508 are employed, adjacent tissue couplers 508 can be axially separated from one another by one or more distances specifically designed to break up standing waves of undesired wave lengths (e.g., wavelengths corresponding to frequencies commonly experienced during exposure to MRI, such as 64 MHz, 128 MHz, or the like). It will be understood that the tissue couplers 508 can be designed to break up standing waves of any suitable wavelength including, for example, wavelengths of 20 MHz, 25 MHz, 30 MHz, 35 MHz, 40 MHz, 45 MHz, 50 MHz, 55 MHz, 60 MHz, 70 MHz, 80 MHz, 90 MHz, 100 MHz, 150 MHz, 200 MHz, 250 MHz, 300 MHz, 350 MHz, 400 MHz, 450 MHz, 500 MHz, or higher. In at least some embodiments, the tissue couplers 508 are designed to break up standing waves that are within a range of 20 MHz to 500 MHz, 20 MHz to 400 MHz, 20 MHz to 200 MHz, or 50 MHz to 150 MHz. It will be understood that each of the preceding wavelength ranges include the endpoints.

The tissue coupler 508, optionally, can be designed such that energy at a particular frequency range more readily passes across the tissue coupler 508 from the conductor 502 to patient tissue. For example, the tissue coupler 508 can include one or more capacitive elements 510 disposed along an outer surface of the lead body, the one or more capacitive elements 510 selected to favor propagation of energy at frequencies commonly experienced during exposure to MRI (e.g., 64 MHz, 128 MHz, or the like) across the tissue coupler 508, while impeding propagation of energy at frequencies commonly used during therapeutic operation of the stimulation system. Accordingly, the tissue coupler 508 can provide a capacitive mechanism for improving or altering the coupling of energy from an insulated lead conductor to surrounding medium.

Optionally, the one or more capacitive elements 510 are selected to favor propagation of energy at frequencies above (or below) frequencies commonly used for therapy during operation of the lead. In some cases, when a plurality of tissue couplers 508 are employed, one or more of the plurality of capacitive elements implemented may be selected to a different frequency, or frequency range, than at least one other of the capacitive elements. Thus, the plurality of tissue couplers 508 may include capacitive elements selected to a plurality of different frequencies at different positions along the lead (or lead extension).

Figure 6A:
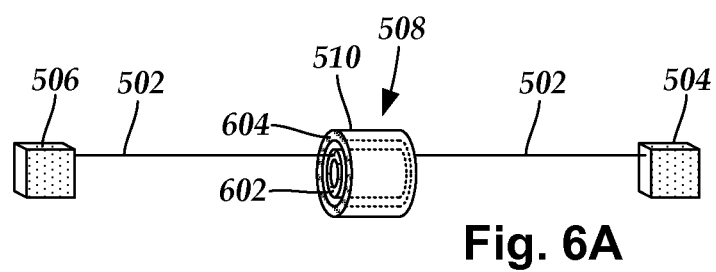
FIG. 6A is a schematic diagram of one embodiment of the tissue coupler of FIG. 5 coupled to the conductor of FIG. 5, the tissue coupler including a capacitor formed from inner and outer conductive members, according to the invention.
Figure 6B:
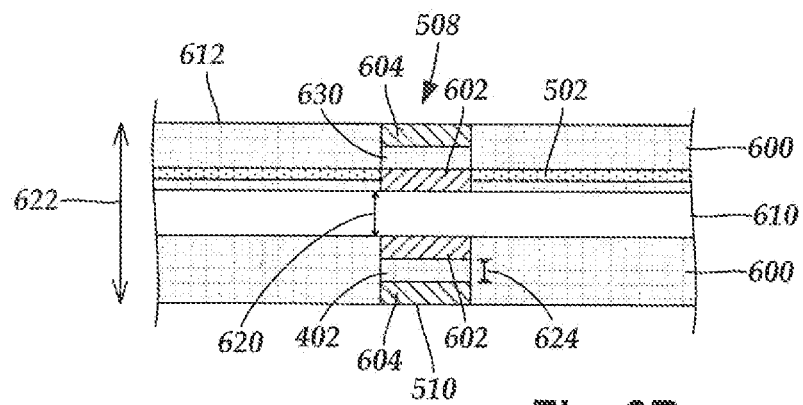
FIG. 6B is a schematic longitudinal cross-sectional view of one embodiment of the tissue coupler of FIG. 6A disposed in a portion of a lead body, according to the invention.

FIG. 6A is a schematic diagram of one embodiment of the tissue coupler 508 coupled to the conductor 502. FIG. 6B is a schematic longitudinal cross-sectional view of one embodiment of the tissue coupler 508 disposed in a portion of a lead body 600 (or lead extension body). The tissue coupler 508 includes one or more inner members 602 and one or more outer members 604. The inner member 602 and the one or more outer members 604 act as the capacitive element 510. The inner member(s) 602 and the outer member(s) 604 can each be any suitable shape. In some cases, one or more of the inner and outer members 602 and 604 have a substantially-planar transverse cross-section. For example, one or more of the inner and outer members 602 and 604 may have a rectangular shape. In at least some embodiments, one or more of the inner and outer members 602 and 604 have a curved shape. For example, one or more of the inner and outer members 602 and 604 may be arc-shaped or C-shaped. In FIGS. 6A-6B, the inner member 602 and the outer member 604 are shown as being cylindrical such that the outer member 604 is concentrically-disposed around the inner member 602.

The conductor 502 is coupled to the one or more inner members 602. The one or more outer members 604 are configured and arranged such that the one or more outer members 604 are at least partially exposed to patient tissue when the lead body 600 is implanted in a patient.

The capacitive element 510 can be disposed along the lead body 600 in any suitable manner. Optionally, the one or more inner members 602 are disposed peripheral to a stylet lumen 610 defined in the lead body 600, with respect to the lead body 600. In some cases, the one or more inner members 602 are at least partially disposed around the stylet lumen 610. In alternate embodiments, the one or more inner members 602 can be disposed along the lead body 600 such that the one or more inner members 602 are disposed peripheral to a central core of the lead body 600. In at least some embodiments, the one or more inner members 602 have a diameter 620 that is not less than a diameter of the stylet lumen 610.

The one or more outer members 604 are disposed along the lead body 600 such that the one or more outer members 604 are peripheral to the one or more inner members 602 with respect to the lead body 600. Optionally, the one or more outer members 604 are disposed along an outer surface 612 of the lead body 600. The one or more outer members 604 can have a diameter 622 that is less than, greater than, or equal to a diameter of the lead body 600.

In some cases, the one or more outer members 604 are isodiametric with the outer surface 612 of the lead body 600. In other cases, the one or more outer members 604 are either inset from, or protruding from, the outer surface 612 of the lead body 600. In at least some embodiments, the one or more inner members 602 are disposed over the outer surface 612 of the lead body 600. The one or more outer members 604 can be either an integral part of the lead body 600 or part of a separate structure that is, optionally, disposed over the lead body 600 at the time of implant. When disposed as part of a separate structure, there may or may not be additional elements for aligning and connecting the one or more inner members 602 and the one or more outer members 604.

When the lead body 600 (or lead extension body) is implanted in the patient, the one or more outer members 604 are in substantial electrical contact with the surrounding tissue but are separated from the one or more inner members 602 by a separation distance 624. The separation distance 624 typically is filled with one or more non-conducting materials (i.e., a dielectric 630). The dielectric 630 prevents accessory current pathways at therapeutic frequencies. Thus, the inner-outer member combination forms a capacitive element that operates at frequencies other than those used for therapy. Accordingly, for at least some non-therapy frequencies the tissue coupler 508 provides a short or leakage path for energy to escape from the conductor 502 into the surrounding tissues.

The dielectric 630 can be formed from any suitable material including, for example, air, the material used to form the lead body 600, or any other non-conductive material suitable for implantation. The material(s) forming the dielectric 630 may be altered to change the electrical behavior (e.g., the capacitance) of the capacitive element 510. Moreover, the thicknesses of the material(s) may be altered to change the electrical behavior of the element in lieu of, or in addition to, changing the material(s) themselves.

The one or more outer members 604 may be disposed fully, or partially, over the one or more inner members 602. The tissue couplers 508 may be disposed at various locations along the length of the lead (or lead extension). Each of the inner and outer members 602 and 604 can have different surface areas from one another. Moreover, when a plurality of tissue couplers 508 are employed, at least one of the tissue couplers 508 can have at least one inner or outer member 602 and 604 with a surface area that is different from the surface area of at least one inner or outer member 602 and 604 of at least one of the other tissue couplers 508. The inner and outer members 602 and 604 may be formed of any biocompatible material including, for example, platinum, platinum-iridium, stainless steel, palladium, or the like.

No more than one conductor is coupled to a given inner member 602. An outer member 604 can be disposed over at least a portion of more than one inner member 602. Optionally, when a first conductor is coupled to a first inner member, at least one of the non-coupled conductors may pass through the center of the first inner member (i.e., beneath the inner member). For certain designs in which there is a high level of coupling between conductors, it may not be necessary to individually couple each conductor to at least one of the inner members 602. Such individual couplings may be identical or unique according to designs that are advantageous in particular applications.

It will be understood that, when a plurality of tissue couplers 508 are employed, each individual tissue coupler 508 need not be identical along the length of the lead (or lead extension). Each individual tissue coupler 508 may be selected (e.g., by varying one or more of dielectric materials, inner or outer member surface area, separation distance between inner and outer members, or the like) or otherwise designed to have a desired local or global effect on the lead (or lead extension).

Individual tissue couplers 508, or an arrangement that includes a plurality of tissue couplers 508, may be chosen such that they are paired to varying tissue types around them upon implantation. For example, a particular design or configuration may be used for portions of the lead (or lead extension) in the epidural space, with a different design or configuration in regions that are tunneled subcutaneously. For example, the spacing between tissue couplers 508 can be tailored to a specific tissue with regards to the wavelength of the tissue. Additionally, the size (or length) of the outer member 604 can be modified, depending on the surrounding tissue and its conductivity.

Optionally, at least one of the one or more inner members 602 of the capacitive elements 510 are formed, at least in part, from one or more of the conductors 502. As discussed above, the one or more conductors 502 can extend along the lead (or lead extension) in any suitable manner. In some cases, one or more of the conductors 502 are coiled (e.g., longitudinally, or the like) along one or more regions of the lead (or lead extension). In which case, the coils themselves may function as the inner member.

Figure 7:
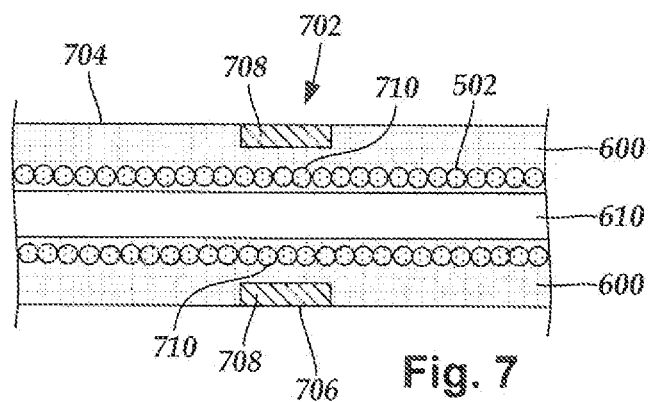
FIG. 7 is a schematic longitudinal cross-sectional view of another embodiment of a tissue coupler disposed in a portion of the lead body of FIG. 6B, the tissue coupler including a capacitor formed from an outer conductive member disposed radially around a coiled region of the conductor of FIG. 5, according to the invention.

FIG. 7 is a schematic longitudinal cross-sectional view of another embodiment of a tissue coupler 702 disposed in a portion of the lead body 600. The tissue coupler 702 includes a capacitive element 706 having one or more outer members 708 disposed radially around at least a portion of the conductor 502, which functions as the inner member 710. The portion of the conductor 502 shown in FIG. 7 is coiled around the stylet lumen 612.

Figure 8:
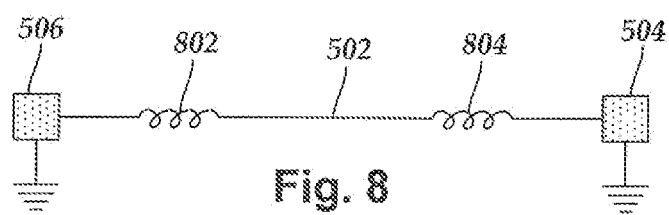
FIG. 8 is a schematic diagram of one embodiment of inductive elements coupled to the conductor of FIG. 5, the inductive elements suitable for altering one or more of the electromagnetic characteristics of the lead of FIGS. 1-3C when the conductor and inductive elements are disposed in the lead, according to the invention.

Turning now of FIG. 8, the elements can include one or more inductive elements disposed along the length of the lead (or lead extension). The inductive elements can be formed from one or more specifically-coiled structures coupled to one or more of the conductors including, for example, one or more regions of the conductors themselves. As discussed above, the inductive elements (as well as the capacitive elements) can be used to break up induced standing waves along the length of the lead (or lead extension).

FIG. 8 is a schematic diagram of one embodiment of inductive elements 802, 804 disposed along the conductor 502. One or more of the inductive elements 802, 804 can be formed as structures coupled to the conductor 502, or as coiled portions of the conductor 502 itself. Inductive elements can be formed from any suitable winding geometry. For example, the conductor 502 can be formed into coils having single layers or multiple layers. Additionally, the inductive elements can be selected based on various characteristics, such as coiling pitch, coil diameter, and the like. Additionally, in at least some embodiments, the conductors 502 can be coiled into one or more regions of more elaborate coiling (see e.g., FIG. 9).

The pitch of the coils of the conductor (i.e., the axial distance between adjacent coils) can vary along one or more regions of the conductor 502. Changing the pitch of the coils along one or more regions of the conductor 502 may alter the electromagnetic properties along all, or a portion, of the lead (or lead extension). The conductors can have one or more regions with relatively-tight pitch ("a tight-pitch region") separated from one another by regions of relatively-wide pitch ("a wide-pitch region"). Any suitable pitch can be used for the tight-pitch regions. For example, the tight-pitch regions can be wound with a single-conductor-diameter pitch (i.e., adjacent coils abut one another). Any suitable pitch can be used for the wide-pitch regions. For example, the wide-pitch regions can be substantially straight, or wound such that the conductors make less than a single revolution around the stylet lumen (610 in FIGS. 6B-7) between adjacent tight-pitch regions.

Increasing the pitch of the coils may increase the inductance of the coil locally (e.g., in proximity to the individual region of the conductor 502 having coils with a tighter pitch). For example, the inductance of a coil may be increased by increasing the cross-sectional area of the coil. Additionally, when used as a portion of a capacitive element, the capacitance of a coil may be increased by creating a longer total wire length for capacitive coupling. Conversely, decreasing the tightness of the coils may decrease the inductance or the capacitance of the coil locally. These local effects (alone or in combination with one or more tissue couplers) may, in turn, affect the global electromagnetic properties of the conductor 502.

Using a variable pitch may reduce at least some effects of RF irradiation. For example, the tight-pitch regions may increase local inductance in proximity to the tight-pitch regions to a desired level. Utilizing a variable pitch may also reduce induced currents due to the discontinuous nature of the winding configuration of the conductors. The tight-pitch regions and the wide-pitch regions may have different electromagnetic properties. Thus, varying the pitches (or the lengths, or both) of one or more of the tight-pitch and wide-pitch regions can be performed to modulate the electromagnetic properties as a function of the position along the length of the lead body (or lead extension body). Additionally, a variable-pitch winding configuration may reduce or eliminate resonant currents developing over substantial portions of the length of the lead (or lead extension). Moreover, a variable-pitch winding configuration may prevent power transmission along structures at radio frequencies. A variable-pitch winding configuration may also reduce common mode coupling by forming distinct patterns of lead electrical parameters for each filar, thereby potentially reducing, or even inhibiting, the flow of common mode currents.

Providing combinations of different winding geometries may also improve device performance under specific circumstances (e.g., frequencies of operation, applied field orientations, or the like) because of the different antenna properties, or impedance properties, or both of the different types of winding geometries. Changing the type of winding geometry (e.g., common-mode current suppression units to co-radial or straight conductor, or the like) adds a new dimension to the variable space for improving the design by using disparate per-unit-length impedance properties or other coupling properties between different winding geometries.

Figure 9:
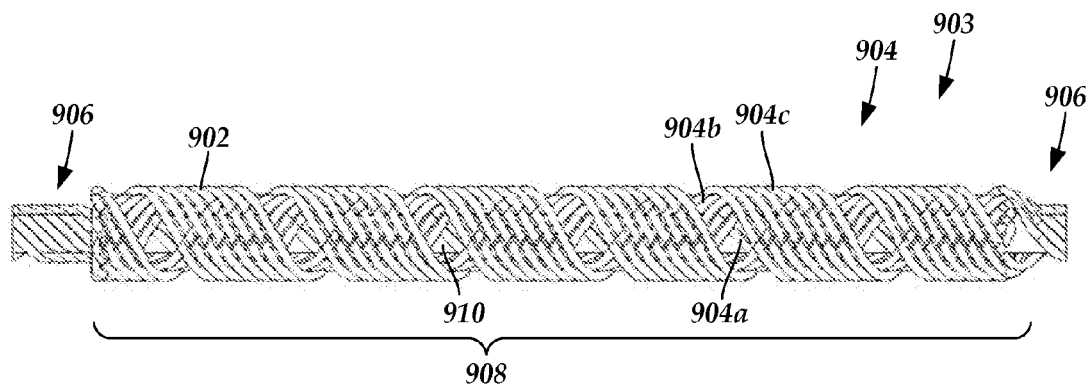
FIG. 9 is a schematic side view of one embodiment of portions of a plurality of conductors configured into common-mode current suppression units, according to the invention.

Turning now to FIG. 9, the conductors can have a winding geometry where conductors are formed into layers. In at least some embodiments one or more of the conductors of the lead (or lead extension) have winding geometries that include a plurality of common-mode current suppression units ("units") arranged in series. Examples of electrical stimulation systems with leads having conductors formed into units are found in, for example, U.S. Patent Application Publication Nos. 2010/0076508; 2010/0094364; and 2010/0256693; 2010/0326701; 2011/0009932; 2011/0046700, all of which are incorporated by reference.

Each unit includes at least three conductor segments that at least partially overlap one another to form a multi-layer region. First, each unit includes a first conductor segment that extends in a first direction along a longitudinal length of an elongated member (e.g., a lead or lead extension) from a beginning point to a first position. Second, each unit includes a second conductor segment that extends from the first position back towards (and possibly past) the beginning point to a second position. Third, each unit includes a third conductor segment that extends in the first direction from the second position to an endpoint. In at least some embodiments, the first position is between the second position and the endpoint. In at least some embodiments, the second position is between the beginning point and the first position. In at least some embodiments, the unit may include a single-layer region flanking at least one end of the multi-layer region.

The units may be electrically continuous such that the endpoint of a first unit is the beginning point of the next consecutive unit. At least one of the beginning points for the series of units may be a terminal or an electrode (or other conductive contact). Likewise, at least one of the endpoints for the series of units may be a terminal or an electrode (or other conductive contact). In preferred embodiments, the conductor segments are each coiled.

In some embodiments, at least one of the first, second, or third conductor segments is substantially straight. In at least some embodiments, the first and third conductor segments are substantially straight and the second conductor segment is coiled. In some other embodiments, all three conductor segments are substantially straight. It will be understood that the term "substantially straight conductor segment" means that the conductor segment is not coiled. A "substantially straight conductor segment" may be curved (but does not make a full revolution around a circumference of the stylet lumen 610 along a length of the conductor segment), particularly when the lead itself is curved (see, for example, FIG. 1).

In some embodiments, the conductor segments are all formed from the same length of conductive material (e.g., wire or the like). The conductors may have a single filament or be multi-filar. In preferred embodiments, the conductors are multi-filar. In some embodiments, two or more of the conductor segments can be individual pieces of conductive material that are electrically coupled (e.g., soldered or welded) together.

In some embodiments, the length of conductor used in the second conductor segment is at least 1.5, 1.75, 1.9, 2, 2.1, 2.25, or 2.5 times the length of either the first conductor segment or the third conductor segment. It will be recognized, however, that this ratio of conductor-segment lengths may vary among embodiments, particularly if the thickness of the conductor or thickness of conductor insulation disposed around the conductors is different for the different segments.

FIG. 9 schematically illustrates one embodiment of a plurality of conductors 902. The conductors 902 include at least one region 903 that has at least one unit, such as unit 904. Each unit includes a first conductor segment 904a, a second conductor segment 904b, and a third conductor segment 904c. In at least some embodiments, conductor insulation is disposed over the conductors 902 to electrically isolate each of the conductors 902 from one another.

Many different numbers of units may be disposed along longitudinal lengths of the conductors 902 including, for example, two, three, four, five, six, seven, eight, nine, ten, twelve, fifteen, twenty, twenty-five, thirty, forty, fifty, or more units. It will be understood that many other numbers of units may be employed as well. When a plurality of units are coupled together in series along a longitudinal length of one or more conductors, the plurality of units form a repeating series of single-layer regions, such as the single-layer regions 906, separated from one another by a multi-layer region, such as the multi-layer region 908.

Figure 10:
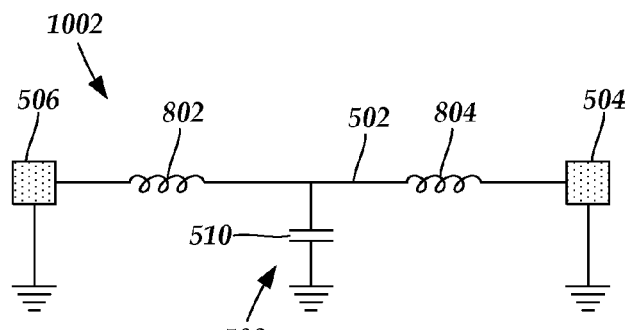
FIG. 10 is a schematic diagram of one embodiment of a circuit formed along the conductor of FIG. 5, the circuit including the tissue coupler of FIG. 5 and the inductive elements of FIG. 8, according to the invention.

Turning now to FIG. 10, circuits can be formed that are capable of altering the electromagnetic characteristics of the lead (or lead extension). The circuits may include, for example, capacitive elements and inductive elements employed in any suitable combination. FIG. 10 is a schematic diagram of one embodiment of a circuit 1002 that includes both the tissue coupler 508 and the inductive elements 802, 804 coupled to the conductor 502.

When a plurality of tissue couplers are employed, the tissue couplers can be in parallel or in series. Similarly, when a plurality of inductive elements are employed, the inductive elements can also be in parallel or in series. Additionally, when a plurality of inductive elements are employed, one or more of the inductive elements can be formed from multiple layers of coils, while one or more of the inductive elements can be formed from a single layer of coils. Furthermore, when a plurality of inductive elements are employed, the inductive elements can be structures coupled to the conductor, or be portions of the conductor itself (e.g., one or more coiled regions, one or more units, or the like or combinations thereof).

Figure 11:
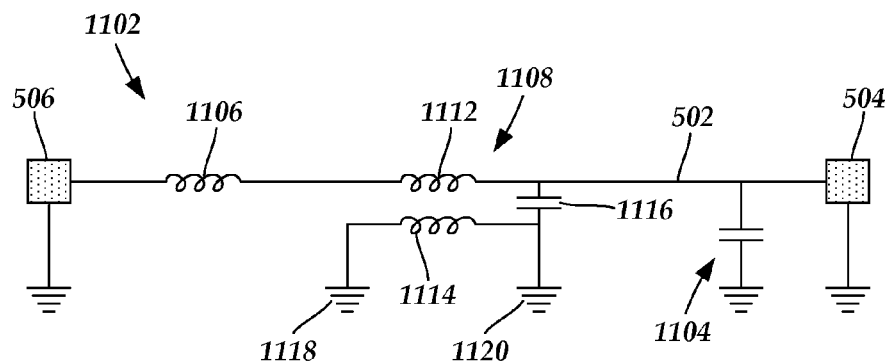
FIG. 11 is a schematic diagram of another embodiment of a circuit formed along the conductor of FIG. 5, the circuit including a plurality of tissue couplers of FIG. 5, a plurality of inductive elements of FIG. 8, and a transformer-like element, according to the invention.

Turning now to FIG. 11, the elements can include one or more transformer-like elements disposed along the length of the lead (or lead extension). FIG. 11 is a schematic diagram of another embodiment of a circuit 1102 with a tissue coupler 1104, an inductive element 1106, and a transformer-like element 1108 coupled to the conductor 502. The transformer-like element 1108 is shown in FIG. 11 as inductors 1112 and 1114, a with inherent capacitance 1116, and grounds 1118 and 1120. In some cases, one or more of the grounds 1118 or 1120 are formed from one or more tissue contact points. The inductors 1112 and 1114 represent inductive coupling to tissue or the outside of the lead via a transformer-like mechanism.

The transformer-like element 1108 can be implemented in any suitable manner including, for example, one or more wires wrapped around another coil (and hence having a coupled flux), a coil that is co-wound with another coil yet terminates via some structure to the tissue (e.g., a transformer), or generally via any set of structures that couple via magnetic fields (e.g., substantially straight wires can do this, even without coiling). The mutual inductance can be positive (same phase) or negative (opposite phase), depending on the winding geometry.

The capacitive element 1116 represents the inherent capacitive coupling of inductively-coupled structures. The capacitive element 1116 can be implemented in any suitable manner including, for example, as an inherent geometrical capacitance, or as an explicit plate-like capacitance. In FIG. 11, the transformer-like element 1108 includes two grounds 1118 and 1120 because mutual inductance in shown in parallel. In alternate embodiments, the transformer-like element can employ a single ground with a wire across the bottom of one of the inductive elements.

Figure 12:
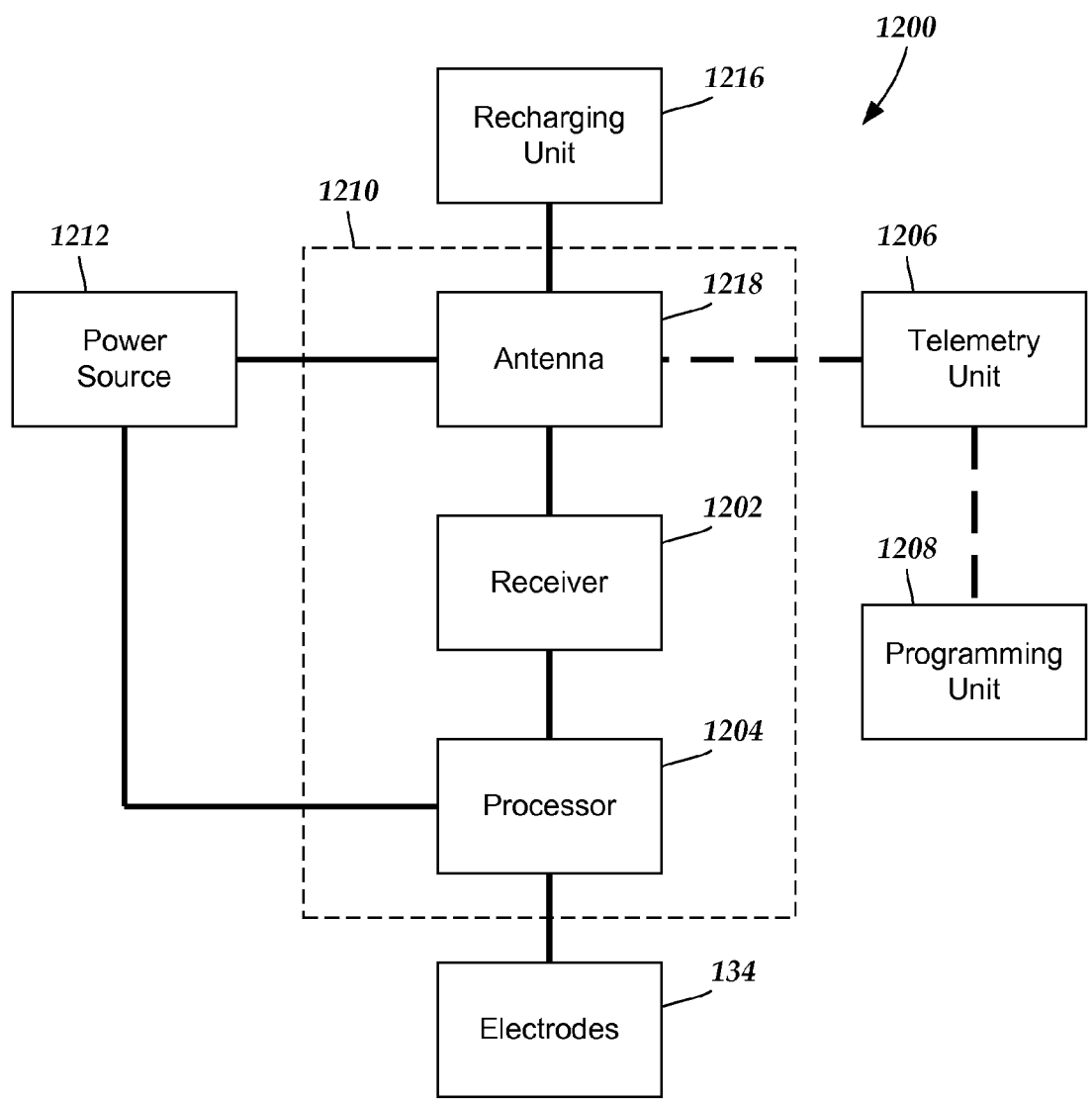
FIG. 12 is a schematic overview of one embodiment of components of a stimulation system, including an electronic subassembly disposed within a control module, according to the invention.

FIG. 12 is a schematic overview of one embodiment of components of an electrical stimulation system 1200 including an electronic subassembly 1210 disposed within a control module. It will be understood that the electrical stimulation system can include more, fewer, or different components and can have a variety of different configurations including those configurations disclosed in the stimulator references cited herein.

Some of the components (for example, power source 1212, antenna 1218, receiver 1202, and processor 1204) of the electrical stimulation system can be positioned on one or more circuit boards or similar carriers within a sealed housing of an implantable pulse generator, if desired. Any power source 1212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1218 or a secondary antenna. The external power source can be in a device that is mounted on the skin of the user or in a unit that is provided near the user on a permanent or periodic basis.

If the power source 1212 is a rechargeable battery, the battery may be recharged using the optional antenna 1218, if desired. Power can be provided to the battery for recharging by inductively coupling the battery through the antenna to a recharging unit 1216 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1204 is generally included to control the timing and electrical characteristics of the electrical stimulation system. For example, the processor 1204 can, if desired, control one or more of the timing, frequency, strength, duration, and waveform of the pulses. In addition, the processor 1204 can select which electrodes can be used to provide stimulation, if desired. In some embodiments, the processor 1204 may select which electrode(s) are cathodes and which electrode(s) are anodes. In some embodiments, the processor 1204 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1208 that, for example, allows modification of pulse characteristics. In the illustrated embodiment, the processor 1204 is coupled to a receiver 1202 which, in turn, is coupled to the optional antenna 1218. This allows the processor 1204 to receive instructions from an external source to, for example, direct the pulse characteristics and the selection of electrodes, if desired.

In one embodiment, the antenna 1218 is capable of receiving signals (e.g., RF signals) from an external telemetry unit 1206 which is programmed by a programming unit 1208. The programming unit 1208 can be external to, or part of, the telemetry unit 1206. The telemetry unit 1206 can be a device that is worn on the skin of the user or can be carried by the user and can have a form similar to a pager, cellular phone, or remote control, if desired. As another alternative, the telemetry unit 1206 may not be worn or carried by the user but may only be available at a home station or at a clinician's office. The programming unit 1208 can be any unit that can provide information to the telemetry unit 1206 for transmission to the electrical stimulation system 1200. The programming unit 1208 can be part of the telemetry unit 1206 or can provide signals or information to the telemetry unit 1206 via a wireless or wired connection. One example of a suitable programming unit is a computer operated by the user or clinician to send signals to the telemetry unit 1206.

The signals sent to the processor 1204 via the antenna 1218 and receiver 1202 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1200 to cease operation, to start operation, to start charging the battery, or to stop charging the battery. In other embodiments, the stimulation system does not include an antenna 1218 or receiver 1202 and the processor 1204 operates as programmed.

Optionally, the electrical stimulation system 1200 may include a transmitter (not shown) coupled to the processor 1204 and the antenna 1218 for transmitting signals back to the telemetry unit 1206 or another unit capable of receiving the signals. For example, the electrical stimulation system 1200 may transmit signals indicating whether the electrical stimulation system 1200 is operating properly or not or indicating when the battery needs to be charged or the level of charge remaining in the battery. The processor 1204 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable electrical stimulation lead comprising:
   a lead body having a distal end, a proximal end, a longitudinal length, and an outer surface;
   a plurality of stimulation electrodes disposed on the distal end of the lead body, wherein the plurality of stimulation electrodes are configured and arranged to stimulate patient tissue during normal operation of the electrical stimulation lead, the plurality of stimulation electrodes comprising a first stimulation electrode;
   a plurality of terminals disposed on the proximal end of the lead body, the plurality of terminals comprising a first terminal;
   a plurality of conductive wires extending along the longitudinal length of the lead body and electrically coupling the plurality of electrodes to the plurality of terminals, the plurality of conductive wires comprising a first conductive wire electrically coupling the first electrode to the first terminal;
   a stylet lumen extending along the longitudinal length of the lead body, the stylet lumen configured and arranged for receiving a stylet; and
   a first tissue coupler disposed along the lead body between the plurality of stimulation electrodes and the plurality of terminals such that the first tissue coupler is physically separate from each of the plurality of stimulation electrodes, the first tissue coupler electrically coupled to the first conductive wire, the first tissue coupler comprising
      a first inner member that is cylindrically-shaped or C-shaped and that is conductive, wherein the first inner member is disposed concentrically over at least a portion of the stylet lumen,
      a non-conductive member disposed adjacent to at least a portion of the conductive first inner member, and
      an outer member that is conductive and that is disposed adjacent to at least a portion of the non-conductive member such that at least a portion of the non-conductive member is sandwiched between the first inner member and the outer member to completely physically separate the outer member from the first inner member, from each of the plurality of conductive wires, and from each of the stimulation electrodes;
   wherein both the first stimulation electrode and the first inner member are conductively coupled to the first conductive wire, and wherein the outer member is disposed along a portion of the outer surface of the lead body such that the outer member is exposed to patient tissue when the lead is implanted in a patient;

wherein the first conductive wire forms less than one revolution around the stylet lumen.

2. The lead of claim 1, wherein the first tissue coupler is one of a plurality of tissue couplers disposed along, the longitudinal length of the lead body, each of the plurality of tissue couplers electrically coupled to a different conductive wire of the plurality of conductive wires.

3. The lead of claim 2, wherein the plurality of tissue couplers are intermittently disposed along the longitudinal length of the lead body.

4. The lead of claim 2, wherein the plurality of tissue couplers comprises a second tissue coupler electrically coupled to a second conductor wire of the plurality of conductor wires, and wherein the second conductive wire extends along the longitudinal length of the lead body such that the first inner member is peripheral to the second conductive wire along the lead body.

5. The lead of claim 4, wherein the first tissue coupler is configured and arranged to operate as a first capacitive element for facilitating propagation of energy at a first frequency through the first tissue coupler from the first conductive wire to patient tissue, wherein the second tissue coupler is configured and arranged to operate as a second capacitive element for facilitating propagation of energy at a second frequency through the second tissue coupler from the second conductive wire to patient tissue, and wherein the first frequency is different than the second frequency.

6. The lead of claim 5, wherein the first frequency and the second frequency are both no less than 20 MHz.

7. The lead of claim 4, wherein the outer member is a first outer member and the non-conductive member is a first non-conductive member, and wherein the second tissue coupler comprises a second non-conductive member.

8. The lead of claim 7, wherein the second tissue coupler comprises a second inner member that is conductive, wherein at least one of the first non-conductive member or the second non-conductive member is disposed adjacent to at least a portion of the second inner member, and wherein the first outer member is disposed adjacent to at least a portion of at least one of the first non-conductive member or the second non-conductive member.

9. The lead of claim 7, wherein the second tissue coupler comprises a second inner member that is conductive, wherein the second non-conductive member is disposed adjacent to at least a portion of the second inner member, and wherein a second outer member that is conductive is disposed adjacent to the second non-conductive member.

10. An electrical stimulation system comprising
the lead of claim 1;
a control module configured and arranged to electrically couple to the proximal end of the lead body, the control module comprising
a housing, and
an electronic subassembly disposed in the housing; and
a connector for receiving the lead, the connector having a proximal end, a distal end, and a longitudinal length, the connector comprising
a connector housing defining a port at the distal end of the connector, the port configured and arranged for receiving the proximal end of the lead body, and
a plurality of connector contacts disposed in the connector housing, the connector contacts configured and arranged to couple to at least one of the plurality of terminals disposed on the proximal end of the lead body.

11. The electrical stimulation system of claim 10, further comprising a lead extension electrically coupling the proximal end of the lead body to the control module, the lead extension comprising
a lead extension body having a distal end, a proximal end, a longitudinal length, and an outer surface;
a plurality of connector contacts disposed on the distal end of the lead extension body;
a plurality of lead extension terminals disposed on the proximal end of the lead extension body;
a plurality of conductors electrically coupling at least one of the connector contacts to at least one of the lead extension terminals, the plurality of conductors extending along the longitudinal length of the lead extension body; and
a first tissue coupler electrically coupled to a first conductor of the plurality of conductors, the first tissue coupler comprising a conductive first inner member, a non-conductive member disposed adjacent to at least a portion of the first inner member, and a conductive outer member disposed adjacent to at least a portion of the non-conductive member such that at least a portion of the non-conductive member is sandwiched between the first inner member and the outer member, wherein the first inner member is electrically coupled to the first conductor, and wherein the outer member is disposed along a portion of the outer surface of the lead extension body such that the outer member is exposed to patient tissue when the lead extension is implanted in a patient.

12. The lead of claim 1, wherein at least a portion of the first conductive wire is coiled longitudinally along at least a portion of the lead body, the coiled portion of the first conductive wire forming an inductive element.

13. The lead of claim 12, further comprising an additional coil that is co-wound with the coiled first conductive wire and that couples with patient tissue when the lead is implanted in the patient.

14. The lead of claim 1, wherein the first tissue coupler is configured and arranged to operate as a capacitive element that is configured and arranged to facilitate propagation of energy through the first tissue coupler from the first conductive wire to patient tissue adjacent to the outer member when the energy has a frequency that is no less than 20 MHz.

15. The lead of claim 1, wherein the first conductive wire is the sole conductive wire of the plurality of conductive wires that is coupled to the first inner member.

16. The lead of claim 1, wherein at least one of the plurality of conductive wires other than the first conductive wire extends through a center of the first inner member.

17. The lead of claim 1, wherein the non-conductive member is disposed concentrically over at least a portion of the first inner member, and the outer member is disposed concentrically over at least a portion of the non-conductive member.

18. The lead of claim 1, wherein the outer member is disposed over a portion of the outer surface of the lead body.

19. The lead of claim 1, wherein the outer member has a surface area that is different from a surface area of the first inner member.

20. The lead of claim 1, wherein the lead body is isodiametric.

* * * * *